United States Patent [19]

Boller et al.

[11] 4,058,477
[45] Nov. 15, 1977

[54] LIQUID CRYSTAL SCHIFFS BASES

[75] Inventors: Arthur Boller, Binningen; Hanspeter Scherrer, Therwil, both of Switzerland

[73] Assignee: Hoffmann-La Roche Inc., Nutley, N.J.

[21] Appl. No.: 611,096

[22] Filed: Sept. 8, 1975

Related U.S. Application Data

[62] Division of Ser. No. 334,292, Feb. 21, 1973, Pat. No. 3,927,064.

[30] Foreign Application Priority Data

Feb. 23, 1972 Switzerland .......................... 2585/72
Jan. 11, 1973 Switzerland ............................ 355/73

[51] Int. Cl.² .......................... C09K 3/34; C02F 1/13
[52] U.S. Cl. .................................. 252/299; 252/63.7; 252/300; 252/408; 350/150; 350/160 LC
[58] Field of Search ............ 252/299, 408, 300, 63.7; 350/150, 160 LC

[56] References Cited

U.S. PATENT DOCUMENTS

| | | | |
|---|---|---|---|
| 3,499,702 | 3/1970 | Goldmacher et al. ................ 252/299 |
| 3,731,986 | 5/1973 | Fergason ...................... 252/408 LC |
| 3,795,436 | 3/1974 | Boller et al. ........................ 252/299 |
| 3,796,479 | 3/1974 | Helfrich et al. ..................... 252/299 |
| 3,815,972 | 6/1974 | Hsieh ................................. 252/299 |
| 3,915,883 | 10/1975 | Vanmeter et al. .................. 252/299 |
| 3,927,064 | 12/1975 | Boller et al. ........................ 252/299 |
| 3,963,313 | 6/1976 | Boller et al. .................. 350/160 LC |

FOREIGN PATENT DOCUMENTS

| | | | |
|---|---|---|---|
| 2,024,269 | 12/1971 | Germany ............................ 252/299 |
| 2,234,522 | 1/1973 | Germany ............................ 252/299 |
| 4,962,390 | 6/1974 | Japan ................................... 252/299 |

OTHER PUBLICATIONS

Boller, A., et al., Proc. of the IEEE, pp. 1002–1003 (Aug. 1972).
Castellano et al., J. Org. Chem., vol. 33, pp. 3501–3504 (1968).
Schadt, M., J. Chem. Phys., vol. 56, No. 4, pp. 1494–1497, (2/15/72).

*Primary Examiner*—Benjamin R. Padgett
*Assistant Examiner*—T. S. Gron
*Attorney, Agent, or Firm*—Samuel L. Welt; Bernard S. Leon; William G. Isgro

[57] ABSTRACT

Liquid crystal substances or compounds of the formula

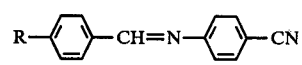

I wherein R is as hereinafter set forth, as well as compositions and electro-optical apparatuses containing them are described.

22 Claims, No Drawings

LIQUID CRYSTAL SCHIFFS BASES

CROSS-REFERENCE TO RELATED APPLICATIONS

This application is a division of U.S. Pat. application Ser. No. 334,292, filed Feb. 21, 1973, now U.S. Pat. No. 3,927,064.

BRIEF SUMMARY OF THE INVENTION

The invention relates to liquid crystalline Schiffs' bases of the formula

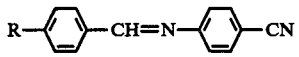
  I wherein R is ethyl, n-propyl, n-butyl, n-pentyl, isohexyl, n-hexyl, n-heptyl or n-octyl.

In another aspect, the invention relates to nematic mixtures for electro-optical uses containing the Schiffs' bases of the invention and to the preparation thereof.

In still another aspect, the invention relates to di-electrics for electro-optical uses and to the preparation thereof. In yet another aspect, the invention relates to an optical cell comprising as a liquid crystal means one or more Schiffs' bases of the invention.

DETAILED DESCRIPTION OF THE INVENTION

The liquid crystalline Schiffs' bases provided by the invention are compounds of the formula

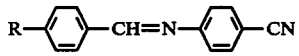
  I wherein R is ethyl, n-propyl, n-butyl, n-pentyl, isohexyl, n-hexyl, n-heptyl or n-octyl, that is, lower alkyl of 2 to 8 carbon atoms.

The compounds of formula I possess, in the liquid crystalline state, a positive anisotropy of the dielectric constants ($\epsilon \parallel > \epsilon\perp$, $\epsilon \parallel$ signifies the dielectric constant along the longitudinal axis of the molecule and $\epsilon\perp$ signifies the dielectric constant perpendicular thereto).

In an electric field, the nematic liquid crystals of the invention orient themselves (because $\epsilon \parallel > \epsilon\perp$) with the direction of their largest dielectric constant (i.e., with their longitudinal axes) parallel to the field direction. This effect is employed, inter alia, in the interaction between embedded molecules and liquid crystal molecules (guest-host interaction) described by J. H. Heilmeier and L. A. Zanoni [Applied Physics Letters 13, 91 (1968)]. A further interesting application of the dielectric field orientation exists in the rotation cell discovered by M. Schadt and W. Helfrich [Applied Physics Letter 18, 127 (1971)].

The electro-optical rotation cell of Schadt et al., supra, comprises essentially a condenser having transparent electrodes whose dielectric is formed essentially from a nematic substance or liquid crystal with a dielectric constant of $\epsilon \parallel > \epsilon\perp$. The longitudinal axes of the liquid crystals are arranged in twisted form between the condenser plates in the fieldless state, the twisting structure being defined by the given wall orientation of the molecules. After the application of an electric potential to the condenser plates, the molecules adjust or orient themselves with their longitudinal axes in the field direction (i.e., perpendicular to the surface of the plates), whereby linear polarized light is no longer rotated in the dielectric (the liquid crystal is uniaxially perpendicular to the surface of the plates). This effect is reversible and can be used for electrically controlling the optical transmissivity of the condenser.

In such "light rotation cells" it is very desirable to use compounds as dielectrics which possess a low melting point and slight viscosity. The compounds previously used for this purpose e.g. p-<(p-ethyloxybenzyliden)amino>benzonitrile (PEBAB) have the disadvantage of first showing nematic properties at relatively high temperatures so that electro-optical apparatuses provided with such liquid crystals have to be heated and possibly thermostatted. Further, said compounds possess a higher viscosity which, for example, leads to considerable disadvantage in electro-optical apparatuses in that operation thereof requires relatively large voltages and long response times.

Unexpectedly, it has now been found that the compounds of formula I of the invention exhibit not only the necessary large or strong positive anisotropy of the dielectric constants but also, individually or in the form of mixtures with one another or with other nematic or non-nematic substances, they are liquid crystalline and exhibit slight viscosity at relatively low temperatures. The use of said compounds is therefore possible with lower voltage and the response time is shorter. A further advantage exhibited by the compounds of formula I is that they can form supercooled nematic phases, which leads to a high stability in the nematic region. This is very important from a practical point of view.

The compounds of formula I of the invention are preferably used in the form of mixtures with one another or with other nematic or non-nematic substances. More preferred mixtures are those whose composition corresponds to a eutectic.

Preferred binary mixtures contain the components in a molar ratio from about 1:10 to about 10:1.

Particularly preferred are mixtures of the following composition:

p-[(p-n-hexylbenzyliden)amino]benzonitrile with p-[(p-n-butylbenzyliden)amino]benzonitrile in a molar ratio of 2:1 to 1:2;

p-[(p-n-propylbenzyliden)amino]benzonitrile with p-[(p-n-hexylbenzyliden)amino]benzonitrile in a molar ratio of 1:2;

p-[(p-n-heptylbenzyliden)amino]benzonitrile with p-[(p-n-butylbenzyliden)amino]benzonitrile in a molar ratio of 2:1;

p-[(p-n-octylbenzyliden)amino]benzonitrile with p-[(p-n-pentylbenzyliden)amino]benzonitrile in a molar ratio of 2:1; and p-[(p-n-butoxybenzyliden)amino]benzonitrile with p-[(p-n-hexylbenzyliden)amino]benzonitrile in a molar ratio of 1:2.

The compounds of formula I of the invention can be prepared in accordance with the processes hereinafter set forth as follows:

a. reacting a compound of the formula

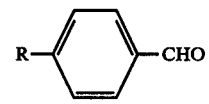
  II wherein R is as hereinbefore described, with p-aminobenzonitrile; or b. dehydrogenating a compound of the formula

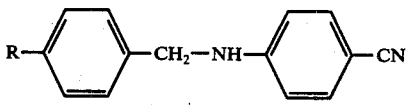

wherein R is as hereinbefore described.

In process embodiment (a) of the invention, a p-loweralkylbenzaldehyde of formula II is reacted with p-aminobenzonitrile. The reaction is conveniently carried out in an inert organic solvent, for example, an alcohol such as methanol, ethanol, or isopropanol, a hydrocarbon such as benzene, toluene or xylene, or a chlorinated hydrocarbon such as chloroform, methylene chloride or ethylene chloride. The reaction is conveniently carried out at a temperature between about 0° C. and 160° C., preferably at between 20° C. and 130° C. The reaction is advantageously carried out at atmospheric pressure. If the reaction is carried out in a water-immiscible solvent, the water formed is advantageously separated by means of a water separator. The reaction is accelerated by the addition of a catalytic amount, up to 5 percent of the aldehyde weight, of a strong inorganic acid, for example, sulfuric acid or hydrochloric acid, or a strong organic acid, for example, methanesulfonic acid, p-toluenesulfonic acid, benzenesulfonic acid, or the like.

In process embodiment (b) of the invention, the compounds of formula I are prepared by dehydrogenating the corresponding compound of formula III. For the dehydrogenation there can be used any dehydrogenating agent known for analogous dehydrogenations, for example, potassium permanganate, selenium dioxide, sodium hypochlorite, ferric chloride, chromic acid or silver oxide. Particularly preferred is manganese dioxide in a chlorinated hydrocarbon, for example, chloroform, methylene chloride or ethylene chloride, or in a hydrocarbon, for example, benzene, toluene or xylene. In accordance with a preferred aspect, manganese dioxide, 8 moles per mol. of compound of formula III, is first heated at reflux in benzene for 5 hours, the water obtained being separated by means of a water separator. The compound of formula III is then added and the mixture heated for an additional 10 hours at reflux, the water formed being again separated. The reaction is advantageously carried out at atmospheric pressure.

The physical properties of the compounds of formula I are set forth in the following Table I:

TABLE I

R—⌬—CH=N—⌬—CN

| | R | Melting Point ° C. | Clearing Point ° C. |
|---|---|---|---|
| A | ethyl | 76.2 – 77.0 | 63.0 – 59.7* |
| B | n-propyl | 64.8 – 65.5 | 77.6 |
| C | n-butyl | 38.1 – 38.7 | 62.6 |
| D | n-pentyl | 45.6 – 46.4 | 75.0 |
| E | n-hexyl | 32.2 – 33.0 | 64.5 |
| F | i-hexyl | 37.7 – 38.5 | 45.3 |
| G | n-heptyl | 32.7 – 33.0 | 72.3 |
| H | n-octyl | 32.5 – 32.8 | 68.8** |

*monotrope
**smectic up to 54.4°

The compounds of formula I are preferably used in the form of mixtures with one another. Mixtures which correspond to a eutectic are especially preferred.

Exemplary of such mixtures are those set forth in the following Table II:

TABLE II

| Mixture (in mol. %) | Melting Point 0° C. | Clearing Point 0° C. |
|---|---|---|
| 33% p-[(p-n-ethylbenzyliden)amino]-)amino]-benzonitrile + 67% p-[(p-n-hexylbenzyliden)amino]benzonitrile | <10 | 54.4 |
| 33% p-[(p-n-propylbenzyliden)amino]-benzonitrile + 67% p-[(p-n-hexylbenzyliden)amino]benzonitrile | <10 | 62.7 |
| 33% p-[(p-n-butyldenzyliden)amino]-benzonitrile + 67% p-[(p-n-hexylbenzyliden)amino]benzonitrile | <10 | 56.8 |
| 33% p-[(p-n-pentylbenzyliden)amino]-benzonitrile + 67% p-[(p-n-hexyl)-benzyliden)amino]benzonitrile | 7 | 61.7 |
| 33% p-[(p-n-heptylbenzyliden)amino]-benzonitrile + 67% p-[(p-n-hexylbenzyliden)amino]benzonitrile | 10 | 63.7 |
| 33% p-[(p-n-octylbenzyliden)amino]-benzonitrile + 67% p-[(p-n-hexylbenzyliden)amino]benzonitrile | 2 | 62.9 |
| 33% p-[(p-n-propylbenzyliden)amino]-benzonitrile + 67% p-[(p-n-heptylbenzyliden)amino]-benzonitrile | 16 | 70.8 |
| 33% p-[p-n-butylbenzyliden)amino]-benzonitrile + 67% p-[(p-n-heptylbenzyliden)amino]-benzonitrile | <10 | 67.5 |
| 33% p-[(p-n-pentylbenzyliden)amino]-benzonitrile + 67% p-[(p-n-heptylbenzyliden)amino]-benzonitrile | 12 | 71.6 |
| 33% p-[(p-n-propylbenzyliden)amino]-)amino] benzonitrile + 67% p-[(p-octylbenzyliden )amino]-benzonitrile | <10 | 65.1 |
| 33% p-[(p-butylbenzyliden)amino]-benzonitrile + 67% p-[(p-n-octylbenzyliden)amino]-benzonitrile | <10 | 64.5 |
| 33% p-[(p-n-pentylbenzyliden)amino]-benzonitrile + 67% p-[(p-n-octylbenzyliden)amino]-benzonitrile | <10 | 68.4 |
| 33% p-[(p-n-benzyliden)amino]-benzonitrile + 67% p-[(p-n-butylbenzyliden)amino]-benzonitrile | <10 | 59.6 |

The compounds of formula I can also be used in the form of mixtures with other known nematic or non-nematic substances. For example, they can be used with the compounds of the formula

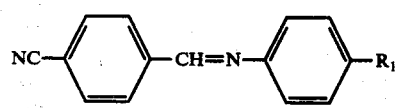

IV wherein $R_1$ is straight-chain lower alkyl of 4 to 7 carbon atoms, or with compounds of the formula

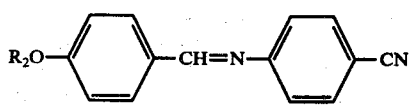

V wherein $R_2$ is straight-chain lower alkyl of 4 to 7 carbon atoms or straight-chain lower alkanoyl of 2 to 6 carbon atoms, or with compounds of the formula

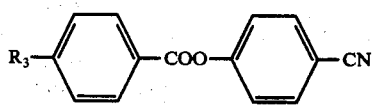

VI wherein $R_3$ is straight-chain lower alkyl of 4 to 8 carbon atoms or straight-chain lower alkoxy of 5 to 8 carbon atoms.

The compounds of formula VI are new compounds and can be prepared, for example, by esterifying a compound of the formula

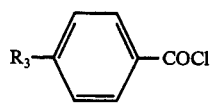

VII wherein R₃ is as previously described, with p-hydroxybenzonitrile in a conventional manner.

The following Examples further illustrate the invention. All temperatures are in degrees Centigrade, unless otherwise mentioned.

EXAMPLE 1

Preparation of p-[(p-ethylbenzyliden)amino]benzonitrile

A mixture of 5.9 g. of p-aminobenzonitrile and 6.7 g. of p-ethylbenzaldehyde in 100 ml. of benzene is treated with 150 mg. of p-toluenesulfonic acid, gassed with nitrogen and heated at reflux for 1 hour (bath temperature 120° C.). The water which forms is separated by means of a water separator. During an additional 1 hour of refluxing, the benzene which condenses in the reflux condenser is led back to the reaction vessel through a layer of 50 g. of aluminum oxide (activity I). After cooling, 2 g. of solid potassium carbonate are added. The mixture is filtered and the filtrate freed from the solvent under vacuum at 50° C. (bath temperature), whereby there remains 11.5 g. of a yellow oil which crystallizes with cooling. Purification is carried out by several recrystallizations from isopropanol to a constant melting point and until by-products are no longer observed by gas chromatogram. The p-[(p-ethylbenzyliden)amino]benzonitrile which is obtained melts at 76.2°–77.0° C. and is liquid crystalline with cooling from 63.0°–59.7° C. UV (ethanol): $\epsilon_{277}$ = 25800 (shoulder at 316 nm). The nuclear magnetic resonance, mass spectrum, infrared and microanalysis data confirm the structure.

EXAMPLE 2

Preparation of p-[(p-n-propylbenzyliden)amino]benzonitrile

A mixture of 5.9 g. of p-aminobenzonitrile and 7.4 g. of p-n-propylbenzaldehyde in 100 ml. of benzene is treated with 150 mg. of p-toluenesulfonic acid and reacted as described in Example 1. After evaporation, there remain 12.5 g. of a yellowish oil which crystallizes with cooling. Purification is carried out by several recrystallizations from isopropanol as described in Example 1. The p-[(p-n-propylbenzyliden)amino]-benzonitrile which is obtained has a melting point of 64.8°–65.5° C. and a clearing point of 77.6° C. UV (ethanol): $\epsilon_{280}$ = 24300 (shoulder at 310 nm). The nuclear magnetic resonance, mass spectrum, infrared and microanalysis data confirm the structure.

EXAMPLE 3

Preparation of p-[(p-n-butylbenzyliden)amino]benzonitrile

A mixture of 11.8 g. of p-aminobenzonitrile and 16.2 g. of p-n-butylbenzaldehyde in 200 ml. of benzene is treated with 300 mg. of p-toluenesulfonic acid and reacted as described in Example 1. After the addition of 3 g. of solid potassium carbonate, the mixture is filtered and evaporated, whereby there are obtained 27.0 g. of a yellow oil which crystallizes with cooling. Purification is carried out by several recrystallizations from isopropanol as described in Example 1. The p-[(p-n-butylbenzyliden)amino]benzonitrile which is obtained has a melting point of 38.1°–38.7° C. and a clearing point of 62.6° C. UV (ethanol): $\epsilon_{280}$ = 24900 (shoulder at 314 nm). The nuclear magnetic resonance, mass spectrum, infrared and microanalysis data confirm the structure.

EXAMPLE 4

Preparation of p-[(p-n-pentylbenzyliden)amino]benzonitrile

A mixture of 5.9 g. of p-aminobenzonitrile and 8.8 g. of p-n-pentylbenzaldehyde in 100 ml. of benzene is treated with 150 mg. of p-toluenesulfonic acid and reacted as described in Example 1. After evaporation, there remain 13.9 g. of a yellow oil which crystallizes with cooling. Purification is carried out by several recrystallizations from isopropanol as described in Example 1. The p-[(p-n-pentylbenzyliden)amino]benzonitrile which is obtained has a melting point of 45.6°–46.4° C. and a clearing point of 75.0° C. UV (ethanol): $\epsilon_{279}$ = 24400 (shoulder at 314 nm). The nuclear magnetic resonance, mass spectrum, infrared and microanalysis data confirm the structure.

EXAMPLE 5

Preparation of p-[(p-n-hexylbenzyliden)amino]benzonitrile

A mixture of 5.9 g. of p-aminobenzonitrile and 9.5 g. of p-n-hexylbenzaldehyde in 100 ml. of benzene is treated with 150 mg. of p-toluenesulfonic acid and reacted as described in Example 1. After evaporation, there remain 14.4 g. of a brownish oil which crystallizes with cooling. Purification is carried out by several recrystallizations from isopropanol as described in Example 1. The p-[(p-n-hexylbenzyliden)amino]benzonitrile which is obtained has a melting point of 32.2°–33.0° C. and a clearing point of 64.5° C. UV (ethanol): $\epsilon_{281}$ = 23500 (shoulder at 310 nm). The nuclear magnetic resonance, mass spectrum, infrared and microanalysis data confirm the structure.

The starting material, i.e., p-n-hexylbenzaldehyde is prepared as follows:

p-n-Hexylbenzaldehyde is prepared according to the method of A. Rieche et al., Chem. Ber. 93, 88 (1960):

To a cooled mixture of 42.5 g. of n-hexylbenzene, 146 ml. of methylene chloride and 48 ml. of titanium tetrachloride there are added dropwise 25.1 g. of dichloromethyl ether with nitrogen gassing and stirring over a period of 20 minutes at 0°–5° C. Then, the mixture is stirred for 15 minutes at 0°–5° C. and for 15 minutes at 20° C. The resulting dark brown solution is poured on to 600 g. of ice and extracted with ether. The organic layer is washed with water, sodium carbonate solution and again with water, dried over sodium sulfate, and the solvent removed under vacuum, whereupon there are obtained 48.7 g. of a brownish oil which, according to gas chromatography, consist of up to 41 percent of n-hexylbenzene, up to 12 percent of o-hexylbenzaldehyde and up to 47 percent of p-n-hexylbenzaldehyde. The mixture is separated by distillation in an efficient column. The pure p-n-hexyl-benzaldehyde boils at 113°–115° C/2.7 mm.

EXAMPLE 6

Preparation of p-[(p-isohexylbenzyliden)amino]benzonitrile

A mixture of 5.9 g. of p-aminobenzonitrile and 9.5 g. of p-isohexylbenzaldehyde in 100 ml. of benzene is treated with 150 mg. of p-toluenesulfonic acid and reacted as described in Example 1. After evaporation, there remain 14.2 g. of a yellow oil which crystallizes with cooling. Purification is carried out by several recrystallizations from isopropanol as described in Example 1. The pure p-[(p-isohexylbenzyliden)amino]benzonitrile has a melting point of 37.7°–38.5° C. and a clearing point of 45.3° C. UV (ethanol): $\epsilon_{280}$ = 23900 (shoulder at 308 nm). The nuclear magnetic resonance, mass spectrum, infrared and microanalysis data confirm the structure.

The starting material, i.e., p-isohexylbenzaldehyde, can be prepared as follows:

To a cooled mixture of 110.3 g. of isohexylbenzene, 380 ml. of methylene chloride and 124.5 ml. of titanium tetrachloride there are added dropwise 65.0 g. of dichloromethyl ether with nitrogen gassing over a period of 20 minutes at 0°–5° C. Then, the mixture is stirred for 15 minutes at 0°–5° C. and for 15 minutes at 20° C. The resulting dark brown solution is poured on to 1555 g. of ice and extracted with ether. After drying and evaporation of the solvent, there remain 121.3 g. of a brownish oil which are pre-purified by normal distillation under vacuum. The fraction distilling at up to 143° C/13 mm (25.7 g.) consists of isohexylbenzene. The fraction distilling at 143°–146° C/13 mm (65.0 g.) consists, according to gas chromatography, of up to 20 percent of o-isohexylbenzaldehyde and up to 78 percent of p-isohexylbenzaldehyde. This mixture is separated by distillation in an efficient column. The pure p-isohexylbenzaldehyde boils at 141°–145° C/14 mm.

EXAMPLE 7

Preparation of p-[(p-n-heptylbenzyliden)amino]benzonitrile

A mixture of 5.9 g. of p-aminobenzonitrile and 10.2 g. of p-n-heptylbenzaldehyde in 100 ml. of benzene is treated with 150 mg. of p-toluenesulfonic acid and reacted as described in Example 1. After evaporation, there remain 15.4 g. of a yellow oil which crystallizes with cooling. Purification is carried out by several recrystallizations from isopropanol as described in Example 1. The p-[(p-n-heptylbenzyliden)amino]benzonitrile which is obtained has a melting point of 32.7°–33.0° C. and a clearing point of 72.3° C. UV (ethanol): $\epsilon_{281}$ = 24100 (shoulder at 310 nm). The nuclear magnetic resonance, mass spectrum, infrared and microanalysis data confirm the structure.

The starting material, i.e., p-n-heptylbenzaldehyde, can be prepared as follows:

To a cooled mixture of 97.3 g. of n-heptylbenzene, 310 ml. of methylene chloride and 102 ml. of titanium tetrachloride there are added dropwise 53.3 g. of dichloromethyl ether with nitrogen gassing over a period of 20 minutes at 0°–5° C. Then, the mixture is stirred for 15 minutes at 0°–5° C. and for 15 minutes at 20° C. The resulting dark brown solution is poured on to 1270 g. of ice and extracted with ether. After drying and evaporation of the solvent, there remain 106.1 g. of a brown oil which is pre-purified by normal distillation under vacuum. The fraction distilling at up to 165° C/17 mm (23.2 g.) consists of n-heptylbenzene. The fraction distilling at 166°–168° C/17 mm. (55.7 g.) consists, according to gas chromatography, of up to 20 percent of o-heptylbenzaldehyde and up to 77 percent of p-n-heptylbenzaldehyde. This mixture is separated by distillation in an efficient column. The pure p-n-heptylbenzaldehyde boils at 166°–168° C/12 mm.

EXAMPLE 8

Preparation of p-[(p-n-octylbenzyliden)amino]benzonitrile

A mixture of 5.9 g. of p-aminobenzonitrile and 10.9 g. of p-n-octylbenzaldehyde in 100 ml. of benzene is treated with 150 ml. of p-toluenesulfonic acid and reacted as described in Example 1. After evaporation, there remain 16.5 g. of a yellow oil which crystallizes with cooling. Purification is carried out by several recrystallizations from isopropanol as described in Example 1. The p-[(p-n-octylbenzyliden)amino]benzonitrile which is obtained has a melting point of 32.5°–32.8° C. and a clearing point of 68.8° C. Up to 54.4° C. the compound is smectic. UV (ethanol): $\epsilon_{280}$ = 24200 (shoulder at 312 nm). The nuclear magnetic resonance, mass spectrum, infrared and microanalysis data confirm the structure.

The starting material, i.e., p-n-octylbenzaldehyde, can be prepared as follows:

To a cooled mixture of 86.8 g. of n-octylbenzene, 255 ml. of methylene chloride and 82.6 ml. of titanium tetrachloride there are added dropwise 43.2 g. of dichloromethyl ether with nitrogen gassing over a period of 20 minutes at 0°–5° C. Then, the mixture is stirred for 15 minutes at 0°–5° C. and for 15 minutes at 20° C. The resulting dark brown solution is poured on to 1030 g. of ice and extracted with ether. After drying and evaporation of the solvent, there remain 96.8 g. of a brown oil which is pre-purified by normal distillation under vacuum. The fraction distilling at up to 160° C/14 mm. (22.9 g.) consists of n-octylbenzene. The fraction distilling at 161°–180° C/14 mm. (52.8 g.) consists, according to gas chromatography, of up to 18 percent of o-n-octylbenzaldehyde and up to 76 percent of p-n-octylbenzaldehyde. This mixture is then separated by distillation with an efficient column. The pure p-n-octylbenzaldehyde boils at 170°–173° C./13 mm.

EXAMPLE 9

Preparation of p-[(p-ethylbenzyliden)amino]benzonitrile 34.7 g. of manganese dioxide [prepared according to J. Org. Chem. 29, 1540 (1964)] are boiled at reflux under a nitrogen stream together with 500 ml. of benzene for 5 hours. The water which forms is separated with a water separator. Then, there are added 11.80 g. of p-[(p-ethylbenzyl)amino]benzonitrile [prepared, for example, by reacting 4-fluorobenzonitrile with p-ethylbenzylamine according to J. Org. Chem. 31, 2319 (1966)]. This mixture is boiled at reflux an additional 10 hours and the formed water separated as described earlier. After cooling, the mixture is filtered through diatomaceous earth, re-washed with benzene and freed from solvent under vacuum (bath temperature 50° C.), whereupon there are obtained 10.5 g. of a yellow oil which crystallizes with cooling. Purification is carried out by several recrystallizations from isopropanol as described in Example 1, whereby there is obtained p-[(p-ethylbenzyliden- )amino]benzonitrile which is identical in all respects with the product obtained according to Example 1.

The following Example illustrates the preparation of a compound of formula VI of the invention:

EXAMPLE A

Preparation of p-n-pentylbenzoic acid p-cyanophenyl ester 3.1 g. of p-hydroxybenzonitrile are dissolved in 40 ml. of absolute pyridine. 6 g. of p-n-pentylbenzoic acid chloride in 20 ml. of benzene are then introduced dropwise at room temperature and the mixture is subsequently stirred overnight. After heating for a short time, the mixture is worked up as described in Example 1 to give 7.5 g. of crude ester. The ester is chromatographed on silica gel using toluene/acetone (19:1). From the uniform fraction there are obtained, after recrystallization from hexane, 2.6 g. of p-n-pentylbenzoic acid p-cyanophenyl ester having a melting point of 60.5° C. and a monotropic clearing point of 56.5° C.

The acid halide starting material, i.e., p-n-pentylbenzoic acid chloride, can be prepared as follows:

15 g. of p-n-pentylbenzoic acid are dissolved in 100 ml. of thionyl chloride and boiled at reflux for 1 hour. The excess thionyl chloride is then removed by distillation and the acid chloride is distilled under high vacuum. The p-n-pentylbenzoic acid chloride which is obtained has a boiling point of 104° C/2 mm.

We claim:

1. A nematic composition which comprises two or more compounds of the formula

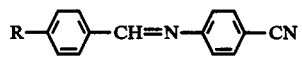

wherein R is ethyl, n-propyl, n-butyl, n-pentyl, isohexyl, n-hexyl, n-heptyl or n-octyl.

2. A nematic composition in accordance with claim 1, which comprises a mixture of p-[(p-ethylbenzyliden)amino]-benzonitrile and p-[(p-n-hexylbenzyliden)amino]benzonitrile.

3. A nematic composition in accordance with claim 1, which comprises a mixture of p-[(p-n-propylbenzyliden)amion]-benzonitrile and p-[(p-n-hexylbenzyliden)amino]benzonitrile.

4. A nematic composition in accordance with claim 1, which comprises a mixture of one part of p-[(p-n-propylbenzyliden)amino]-benzonitrile and two parts of p-[(p-n-hexylbenzyliden)amino]benzonitrile.

5. A nematic composition in accordance with claim 1, which comprises a mixture of p-[(p-n-butylbenzyliden)amino]-benzonitrile and p-[(p-n-hexylbenzyliden)amino]benzonitrile.

6. A nematic composition in accordance with claim 1, which comprises a mixture of p-[(p-n-pentylbenzyliden)amino]-benzonitrile and p-[(p-n-hexylbenzyliden)amino]benzonitrile.

7. A nematic composition in accordance with claim 1, which comprises a mixture of p-[(p-n-heptylbenzyliden)amino]-benzonitrile and p-[(p-n-hexylbenzyliden)amino]benzonitrile.

8. A nematic composition in accordance with claim 1, which comprises a mixture of p-[(p-n-octylbenzyliden)amino]-benzonitrile and p-[(p-n-hexylbenzyliden)amino]benzonitrile.

9. A nematic composition in accordance with claim 1, which comprises a mixture of p-[(p-n-propylbenzyliden)amino]benzonitrile and p-[(p-n-heptylbenzyliden)amino]benzonitrile.

10. A nematic composition in accordance with claim 1, which comprises a mixture of p-[(p-n-butylbenzyliden)amino]benzonitrile and p-[(p-n-heptylbenzyliden)amino]benzonitrile.

11. A nematic composition in accordance with claim 1, which comprises a mixture of p-[(p-n-pentylbenzyliden)amino]benzonitrile and p-[(p-n-heptylbenzyliden)amino]benzonitrile.

12. A nematic composition in accordance with claim 1, which comprises a mixture of p-[(p-n-propylbenzyliden)amino]benzonitrile and p-[(p-n-octylbenzyliden)amino]benzonitrile.

13. A nematic composition in accordance with claim 1, which comprises a mixture of p-[(p-n-butylbenzyliden)amino]benzonitrile and p-[(p-n-octylbenzyliden)amino]benzonitrile.

14. A nematic composition in accordance with claim 1, which comprises a mixture of p-[(p-n-pentylbenzyliden)amino]benzonitrile and p-[(p-n-octylbenzyliden)amino]benzonitrile.

15. A nematic composition which comprises a Schiffs' base of the formula

wherein R is ethyl, n-propyl, n-butyl, n-pentyl, n-hexyl, isohexyl, n-heptyl or n-octyl, or mixtures thereof and one or more nematic compounds having a positive anisotropy.

16. A nematic composition which comprises a compound of the formula

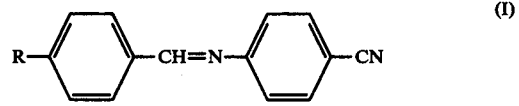

wherein R is ethyl, n-propyl, n-butyl, n-pentyl, n-hexyl, isohexyl, n-heptyl or n-octyl, or mixtures thereof, and a compound of the formula

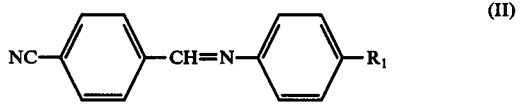

wherein $R_1$ is straight-chain lower alkyl of 4 to 7 carbon atoms.

17. A nematic composition which comprises a compound of the formula

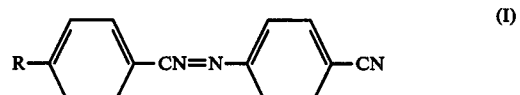

wherein R is ethyl, n-propyl, n-butyl, n-pentyl, n-hexyl, isohexyl, n-heptyl or n-octyl, or mixtures thereof, and a compound of the formula

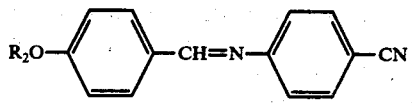
(II)

wherein $R_2$ is straight-chain lower alkyl of 4 to 7 carbon atoms or straight-chain lower alkanoyl of 2 to 8 carbon atoms.

18. A nematic composition which comprises a compound of the formula

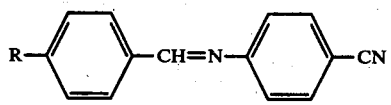
(I)

wherein R is ethyl, n-propyl, n-butyl, n-pentyl, n-hexyl, isohexyl, n-heptyl or n-octyl, or mixtures thereof, and a compound of the formula

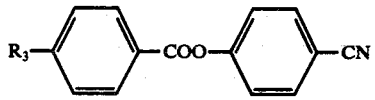
(II)

wherein $R_2$ is straight-chain lower alkyl of 4 to 8 carbon atoms or straight-chain lower alkoxy of 5 to 8 carbon atoms.

19. A nematic composition in accordance with claim 16, wherein the compound of formula I is p-[(p-n-hexylbenzyliden)amino]benzonitrile.

20. A nematic composition in accordance with claim 17, wherein the compound of formula I is p-[(p-n-hexylbenzyliden)amino]benzonitrile.

21. A nematic composition in accordance with claim 18, wherein the compound of formula I is p-[(p-n-hexylbenzyliden)amino]benzonitrile.

22. A dielectric for electro-optical purposes, which comprises a nematic Schiffs' base of the formula

wherein R is ethyl, n-propyl, n-butyl, n-pentyl, isohexyl, n-hexyl, n-heptyl or n-octyl, or mixtures thereof and one or more nematic compounds having positive anisotropy.

* * * * *

UNITED STATES PATENT AND TRADEMARK OFFICE
CERTIFICATE OF CORRECTION

PATENT NO. : 4,058,477
DATED : November 15, 1977
INVENTOR(S) : Arthur Boller et al.

It is certified that error appears in the above-identified patent and that said Letters Patent are hereby corrected as shown below:

Column 9, claim 3, line 45,   ")amion]-benzonitrile" should be:

)amino]-benzonitrile

Signed and Sealed this

Sixth Day of February 1979

[SEAL]

Attest:

RUTH C. MASON
Attesting Officer

DONALD W. BANNER
Commissioner of Patents and Trademarks